(12) United States Patent
Matsunami et al.

(10) Patent No.: US 10,292,853 B2
(45) Date of Patent: May 21, 2019

(54) MEDICAL INSTRUMENT

(71) Applicant: SOSAIKOUSEIKAI CLINICAL FOUNDATION MATSUNAMI RESEARCH PARK, Gifu (JP)

(72) Inventors: Hidetoshi Matsunami, Gifu (JP); Kuniaki Saito, Aichi (JP); Yushi Matuo, Osaka (JP); Masao Takemura, Gifu (JP)

(73) Assignee: SOSAIKOUSEIKAI CLINICAL FOUNDATION MATSUNAMI RESEARCH PARK, Gifu (JP)

( * ) Notice: Subject to any disclaimer, the term of this patent is extended or adjusted under 35 U.S.C. 154(b) by 0 days.

(21) Appl. No.: 15/129,671

(22) PCT Filed: Mar. 12, 2015

(86) PCT No.: PCT/JP2015/057361
§ 371 (c)(1),
(2) Date: Sep. 27, 2016

(87) PCT Pub. No.: WO2015/146612
PCT Pub. Date: Oct. 1, 2015

(65) Prior Publication Data
US 2017/0135835 A1 May 18, 2017

(30) Foreign Application Priority Data
Mar. 28, 2014 (JP) ................. 2014-068503

(51) Int. Cl.
*A61M 5/00* (2006.01)
*A61F 5/00* (2006.01)
*A61F 2/04* (2013.01)

(52) U.S. Cl.
CPC ...... *A61F 5/0076* (2013.01); *A61F 2002/045* (2013.01); *A61F 2210/0004* (2013.01);
(Continued)

(58) Field of Classification Search
CPC ............. A61F 5/0076; A61F 2002/045; A61F 2210/0004; A61F 2250/0031; A61F 2250/0067; A61F 2250/0098
(Continued)

(56) References Cited

U.S. PATENT DOCUMENTS 5,820,584 A 10/1998 Crabb
6,740,121 B2 5/2004 Geitz
(Continued)

FOREIGN PATENT DOCUMENTS

EP 2 561 839 A1 2/2013
JP 2005-500127 A 1/2005
(Continued)

OTHER PUBLICATIONS

International Search Report issued in Application No. PCT/JP2015/057361 dated Jun. 9, 2015.
(Continued)

*Primary Examiner* — Andrew J Mensh
(74) *Attorney, Agent, or Firm* — Pearne & Gordon LLP

(57) ABSTRACT

A medical device according to the present invention is to be arranged in a lumen of a gastrointestinal tract. The medical device includes: at least one cylindrical part which is opened at least one end thereof; and at least one attachment part which is arranged on at least one portion of the cylindrical part and is configured such that the medical device is attachable to the lumen of the gastrointestinal tract. The cylindrical part is configured to be arrangeable along at least one portion of the gastrointestinal tract, and at least one portion of a side surface of the cylindrical part is configured to be followable to a shape of an inner wall of the gastrointestinal tract.

11 Claims, 15 Drawing Sheets

(52) U.S. Cl.
CPC ............ *A61F 2250/0031* (2013.01); *A61F 2250/0067* (2013.01); *A61F 2250/0098* (2013.01)

(58) Field of Classification Search
USPC ............................................. 604/8
See application file for complete search history.

(56) References Cited

U.S. PATENT DOCUMENTS

| | | | |
|---|---|---|---|
| 2003/0040804 A1 | 2/2003 | Stack | |
| 2004/0148034 A1* | 7/2004 | Kagan | A61F 2/04 623/23.65 |
| 2004/0220682 A1* | 11/2004 | Levine | A61F 5/0076 623/23.65 |
| 2005/0125020 A1 | 6/2005 | Meade | |
| 2007/0293885 A1* | 12/2007 | Binmoeller | A61F 5/0076 606/191 |
| 2011/0087146 A1 | 4/2011 | Ryan | |
| 2011/0137428 A1 | 6/2011 | Terliue | |
| 2011/0207994 A1* | 8/2011 | Burrell | A61F 5/003 600/37 |
| 2012/0004676 A1* | 1/2012 | Vargas | A61F 5/0076 606/153 |
| 2012/0095483 A1* | 4/2012 | Babkes | A61F 5/0079 606/153 |

FOREIGN PATENT DOCUMENTS

| | | |
|---|---|---|
| JP | 2007-513685 A | 5/2007 |
| JP | 2009-538218 A | 11/2009 |

OTHER PUBLICATIONS

Extended European Search Report for 15 76 9822 dated Nov. 21, 2017.

* cited by examiner

STOMACH NON-LINING PART

INTESTINAL TRACT NON-LINING PART

STOMACH LINING PART

INTESTINAL TRACT LINING PART

STOMACH NON-LINING PART

INTESTINAL TRACT NON-LINING PART

STOMACH LINING PART

INTESTINAL TRACT LINING PART

STOMACH NON-LINING PART

INTESTINAL TRACT NON-LINING PART

STOMACH LINING PART

INTESTINAL TRACT LINING PART

MEDICAL INSTRUMENT

TECHNICAL FIELD

The present invention relates to a medical device which is to be arranged in a lumen of a gastrointestinal tract.

BACKGROUND ART

There is known, as a medical device in treatment of obesity, a medical device having a sleeve and an anchor, which is to be arranged in a lumen of a gastrointestinal tract to suppresses the digestion and absorption (Patent Literature 1).

When the medical device is used, however, a motility of a gastrointestinal tract, such as peristaltic-movement, is inhibited by the device, and the contact of a food with a gastrointestinal mucosa is blocked. As a result, the atrophy of the gastrointestinal mucosa occurs, and then the atrophied membrane is not recovered. In addition, a problem arises in that the rigid medical device persistently presses an inner wall of the gastrointestinal tract so that the mucous membrane may have a risk to fall into pressure necrosis.

CITATION LIST

Patent Literature

[PTL 1] JP 2007-513685 A

SUMMARY OF INVENTION

Technical Problem

The present invention has been made to solve the problems as described above, and an object of the present invention is to provide a medical device which can suppress the digestion and absorption, and can prevent the atrophy of a gastrointestinal mucosa.

Solution to Problem

According to the present invention, there is provided a medical device to be arranged in a lumen of a gastrointestinal tract. The medical device includes: at least one cylindrical part which is opened at least one end thereof; and at least one attachment part which is arranged on at least one portion of the cylindrical part and is configured such that the medical device is attachable to the lumen of the gastrointestinal tract. The cylindrical part is configured to be arrangeable along at least one portion of the gastrointestinal tract, and at least one portion of a side surface of the cylindrical part is configured to be followable to a shape of an inner wall of the gastrointestinal tract.

In one embodiment of the present invention, at least one portion of the cylindrical part is formed of a fiber.

In one embodiment of the present invention, at least one portion of the cylindrical part has a net form.

In one embodiment of the present invention, at least one portion of the cylindrical part is configured to be expandable in a diametrical direction of the cylindrical part.

In one embodiment of the present invention, the cylindrical part is configured to be unstretchable in a longitudinal direction of the cylindrical part.

Advantageous Effects of Invention

The medical device of the present invention can suppress the digestion and absorption, and can prevent the atrophy of a gastrointestinal mucosa.

DESCRIPTION OF EMBODIMENTS

Embodiments of the present invention are hereinafter described with reference to the drawings. However, the present invention is not limited to these embodiments.

A-1. Whole Configuration of Medical Device

Figure 1:
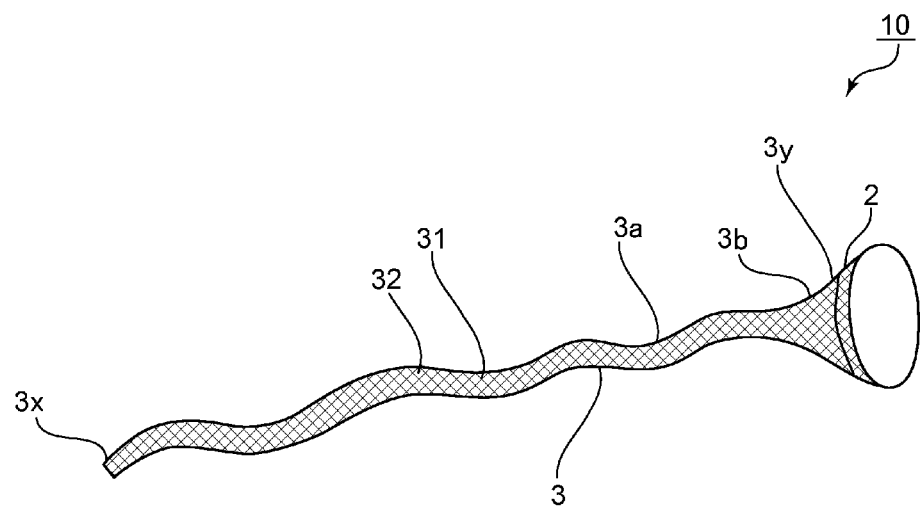
FIG. 1 is a schematic view of a medical device according to one embodiment of the present invention.

FIG. 1 is a schematic view of a medical device 10 according to one embodiment of the present invention. The medical device 10 includes at least one attachment part 2 and at least one cylindrical part 3. In the illustrated example, the medical device 10 includes one attachment part 2 and one cylindrical part 3.

The cylindrical part 3 is typically opened at least one end thereof. In the illustrated example, the cylindrical part 3 (that is, an end 3x on the opposite side to the attachment part 2 and an end 3y on the attachment part 2 side) is opened at both ends thereof.

The attachment part 2 is arranged on at least one portion of the cylindrical part 3. The attachment part 2 may be arranged at any appropriate position of the cylindrical part 3. In the illustrated example, the attachment part 2 is arranged at the end 3y of the cylindrical part 3.

The attachment part 2 and the cylindrical part 3 may be integrally configured, or may be configured in combination as different members. In the example illustrated in FIG. 1, the attachment part 2 and the cylindrical part 3 are integrally configured. That is, a predetermined zone of the end of the cylindrical part 3 is the attachment part 2.

The attachment part 2 typically has any appropriate configuration in which the medical device 10 is attachable to a lumen of a gastrointestinal tract through the attachment part 2. The attachment part 2 may be attachable to the lumen of the gastrointestinal tract through another member, or may be directly attachable to the lumen of the gastrointestinal tract (including a mechanism in which the attachment part 2 may be wearable through oral administration). An example of the configuration in which the attachment part 2 may be directly attachable to the lumen of the gastrointestinal tract is a stent.

The attachment part 2 preferably has any appropriate configuration in which the medical device is attachable to a lumen of a gastrointestinal tract through another member. When the attachment part 2 has the configuration described above, the medical device can be arranged and removed in a simpler manner. As the result, it becomes easier to return the lumen of the gastrointestinal tract to the state before the use of the medical device at an appropriate timing. Examples of another member described above include a thread (e.g., a suture thread), a stapler, a hook, a clip, and a combination thereof.

The cylindrical part 3 is configured to be arrangeable along at least one portion of the gastrointestinal tract. Any appropriate configuration may be adopted as the configuration described above. The cylindrical part 3 is typically bendable in a longitudinal direction.

At least one portion of a side surface of the cylindrical part 3 is configured to be followable to a shape of an inner wall of a gastrointestinal tract. The phrase "followable to a shape of an inner wall of a gastrointestinal tract" used herein means that when the medical device is used, the device is tightly attachable to the inner wall of the gastrointestinal tract in accordance with a motility of the gastrointestinal tract.

Any appropriate length may be adopted as a length of the longitudinal direction of the cylindrical part 3. The length is, for example, from 30 cm to 9 m. When the length of the longitudinal direction of the cylindrical part 3 falls within the range described above, the medical device can easily be arranged in a lumen of a gastrointestinal tract without impairing a suppressive effect on the digestion and absorption to be obtained by the medical device. A shape, an area, and a length of each of members used herein refer to the shape, the area, and the length of the medical device in the original state, respectively, unless otherwise specified.

When the medical device 10 is used, the cylindrical part 3 may be stretchable in the longitudinal direction or may be unstretchable in the direction. The cylindrical part 3 is preferably unstretchable in the longitudinal direction. When the cylindrical part 3 is unstretchable in the longitudinal direction, the position of the end 3x of the cylindrical part 3 is stable during the use of the medical device 10. The term "unstretchable" used herein means, for example, that a length at maximum elongation is 110% or less relative to a length before elongation.

At least one portion of the cylindrical part 3 is typically deformable in accordance with a motility of a gastrointestinal tract. When the device has the configuration described above, the followability of the cylindrical part to a shape of an inner wall of the gastrointestinal tract is improved, and a physical stimulus given to the inner wall of the gastrointestinal tract by a digested content increases. As a result, a preventive effect on the atrophy of the gastrointestinal mucosa is improved.

At least one portion of the cylindrical part 3 is typically expandable in the diametrical direction of the cylindrical part 3 in accordance with a motility of a gastrointestinal tract. Any appropriate rate may be adopted as a rate of a cross-sectional area at maximum expansion of at least one cross section of the cylindrical part 3 to a cross-sectional area in the cross section. An example of the rate is 200% or more. When the device has the configuration described above, the cylindrical part can more surely follow a shape of the inner wall of the gastrointestinal tract at the time of, for example, the expansion of the gastrointestinal tract in the cross-sectional direction during the passage of a digested content through the gastrointestinal tract. As a result, the preventive effect on the atrophy of the gastrointestinal mucosa is improved. Meanwhile, the rate is, for example, 10,000% or less.

At least one portion of the cylindrical part 3 is typically reducible in the diametrical direction of the cylindrical part 3 in accordance with a motility of a gastrointestinal tract. Any appropriate rate may be adopted as a rate of a cross-sectional area at maximum reduction of at least one cross section of the cylindrical part 3 to a cross-sectional area in the cross section. An example of the rate is 75% or less. When the cylindrical part has the configuration described above, a preventive effect on the atrophy of the gastrointestinal mucosa is improved because the cylindrical part can more surely follow a shape of an inner wall of the gastrointestinal tract at the time of the reduction of the gastrointestinal tract in the cross-sectional direction in response to the motility of the gastrointestinal tract. Meanwhile, the rate is, for example, 0.5% or more.

A shape of the cross section of the cylindrical part 3 may be any appropriate shape. An example of the shape is a substantially circular shape.

In the illustrated example, the cylindrical part 3 has a fixed region 3a in which the cross-sectional area of the cross section of the cylindrical part 3 is substantially fixed, and an enlargement region 3b in which the cross-sectional area of the cross section of the cylindrical part 3 increases. The fixed region 3a extends in the direction from the end 3x toward the end 3y. The enlargement region 3b extends from the end of the fixed region 3a on the end 3y side toward the end 3y. In the enlargement region 3b, a cross-sectional area of the cross section of the cylindrical part 3 increases toward the end 3y in a tapered manner. When the cylindrical part 3 has the fixed region 3a, the cylindrical part can more easily be arranged along at least one portion of the gastrointestinal tract. When the cylindrical part 3 has the enlargement region 3b, the medical device can be arranged in a lumen of the gastrointestinal tract in a more stable manner.

A length of the fixed region 3a is, for example, 60% or more, preferably 80% or more relative to a length of the whole of the cylindrical part 3.

Any appropriate cross-sectional area may be adopted as a cross-sectional area of the fixed region 3a. The cross-sectional area is, for example, from 2 $cm^2$ to 12 $cm^2$. When the fixed region has the configuration described above, a preventive effect on the atrophy of the gastrointestinal mucosa is improved, and the cylindrical part can more easily be arranged along at least one portion of the gastrointestinal tract.

The cylindrical part 3 is typically configured so as to cause some of a digestive fluid and/or a digested content to permeate therethrough. When the cylindrical part 3 has the configuration described above, the digestive fluid and the digested content are not completely bypassed during the use of the medical device, and hence rapid transfer of a food to the bottom of the small intestine can be reduced. As a result, a dumping syndrome, which occurs after eating on a subject, can be effectively prevented. The dumping syndrome refers to a symptom which is caused by rapid feeding of a food to the bottom of the small intestine without the remaining of the food in the stomach of the subject after eating, and the symptom is associated with, for example, nausea, vomiting, weakness, palpitation, and perspiration. Accordingly, such uncomfortable symptoms which the subject receives are reduced, and treatment of obesity can be more comfortably performed. In addition, a state closer to a physiological condition can be realized during the use of the medical device.

The cylindrical part 3 may have any appropriate shape. At least one portion of the cylindrical part 3 may have, for example, a net form (FIG. 1 and FIG. 2), a strip form (FIG. 3), a slit form (FIG. 4), a perforated form (FIG. 5), an irregular form (FIG. 6), a membrane form (FIG. 7), or a combination thereof. Preferably, at least one portion of the cylindrical part 3 has a net form, a strip form, a slit form, a perforated form, or a combination thereof. More preferably, at least one portion of the cylindrical part 3 has a net form. The embodiment of FIG. 1 (embodiment in which the whole of the cylindrical part 3 has a net form) is mainly described herein, and any other embodiment is simply described regarding only its characteristic part later.

When at least one portion of the cylindrical part 3 has a net form, a strip form, a slit form, a perforated form, or a combination thereof, the cylindrical part easily deforms, and the shape followability to an inner wall of a gastrointestinal tract is improved. As a result, suppression of a motility of the gastrointestinal tract is more effectively prevented, and a physical stimulus to the inner wall of the gastrointestinal tract further increases. Therefore, a preventive effect on the atrophy of the gastrointestinal mucosa is improved. In addition, some of a digestive fluid and/or a digested content can be easily caused to permeate through the cylindrical part, and hence a dumping syndrome can be effectively prevented.

In addition, when at least one portion of the cylindrical part 3 has a net form, a strip form, a slit form, or a combination thereof, a period for which the medical device exhibits a suppressive effect on the digestion and absorption can be easily adjusted. The adjustment is performed by using a biodegradable material as a material which constitutes the cylindrical part, and adjusting, for example, an area and/or aperture ratio of a net form, a strip form, and/or a slit form which constitutes the cylindrical part.

In addition, when at least one portion of the cylindrical part 3 has a net form, the cylindrical part is hardly twisted in the gastrointestinal tract, and hence the occurrence of an occlusion of the gastrointestinal tract can be easily prevented. In addition, the cylindrical part can be easily made unexpandable in the longitudinal direction.

Any appropriate rate may be adopted as a rate of an area of a net form portion to that of the whole of the cylindrical part 3. The rate is, for example, from 60% to 100%.

As a shape of the net form, there is given, for example, a shape of a web form, a grid form, a hauberk form, or a combination thereof. In the illustrated example, the shape is of a web form. Any appropriate shape may be adopted as the shape of the hauberk form. Examples of the shape of the hauberk form include shapes of 4 to 1, 6 to 1, and/or 4 to 2.

An aperture 32 of a net 31 may have any appropriate shape. In the illustrated example, the aperture 32 has a substantially rhombus shape. The aperture 32 may have a substantially multiangular shape or a substantially circular shape. An example of the substantially multiangular shape is a substantially quadrangular shape. Examples of the substantially quadrangular shape include a substantially rectangular shape (including a square shape) and a substantially rhombus shape. A substantial quadrangle, which constitutes the substantially quadrangle shape, is preferably a substantial quadrangle in which one of two diagonal lines is substantially parallel to the longitudinal direction of the cylindrical part 3. When at least some of the apertures 32 have substantially multiangular shapes, the cylindrical part can be easily made unexpandable in the longitudinal direction.

Any appropriate aperture ratio may be adopted as an aperture ratio of the net 31 depending on a target diet effect, a rate of an area of the net form portion, and the like. For example, when the rate of the area is 100% (i.e., when the whole of the cylindrical part 3 has a net form), the aperture ratio of the net 31 is, for example, from 1% to 99.9%, preferably from 40% to 99%, more preferably from 60% to 95%. When the aperture ratio falls within the range described above, the atrophy of the gastrointestinal mucosa can be effectively prevented. In addition, the permeability of the cylindrical part increases and hence a dumping syndrome can be effectively prevented. In addition, a sufficient suppressive effect on the digestion and absorption can be achieved by the medical device.

A size of an aperture of the net 31 may be of from a micron order to a millimeter order depending on the purpose. That is, the net 31 may be literally a net or substantially a porous film.

The attachment part 2 may have any appropriate shape. Typically, the attachment part 2 is integrally configured with the cylindrical part 3, and hence the attachment part 2 may have the same shape as that of the cylindrical part 3. Accordingly, the attachment part 2 has, for example, a net form (FIG. 1), a strip form, a slit form, a perforated form, an irregular form, a membrane form, or a combination thereof. The attachment part 2 preferably includes a net form, a strip form, a slit form, a perforated form, and a combination thereof. The attachment part 2 more preferably includes a net form. In the example illustrated in FIG. 1, the attachment part 2 is integrally configured with the cylindrical part 3 having a net form, and hence the whole of the attachment part 2 has a net form. When the attachment part 2 has a net form, a strip form, a slit form, a perforated form, or a combination thereof, the medical device may be arranged and removed in a simpler manner. As the result, it becomes easier to return the lumen of the gastrointestinal tract to the state before the use of the medical device at an appropriate timing. In FIG. 1, an embodiment in which the attachment part 2 has a net form is illustrated. In each of FIG. 2 to FIG. 7, an embodiment in which the attachment part 2 has a membrane form is illustrated.

A-2. Constituent Material of Medical Device

Any appropriate material may be adopted as a material which constitutes the medical device 10. Examples of the material include a biodegradable material and a non-biodegradable material.

Any appropriate biodegradable material may be adopted as the biodegradable material. Examples of the biodegradable material include a biodegradable synthetic polymer, a biodegradable material derived from biomass, and a combination thereof. Any appropriate biodegradable synthetic polymer may be adopted as the biodegradable synthetic polymer. Examples of the biodegradable synthetic polymer include a glycolide-based polymer, a dioxanone-based polymer, a lactide-based polymer, and a combination thereof. The biodegradable synthetic polymer is preferably a glycolide polymer, a glycolide-lactide copolymer, a glycolide-trimethylene carbonate copolymer, a glycolide-dioxanone-trimethylene carbonate copolymer, a glycolide-epsilon-caprolactone copolymer, a dioxanone polymer, or a combination thereof. The biodegradable synthetic polymer is more preferably a glycolide polymer, a glycolide-lactide copolymer, a glycolide-trimethylene carbonate copolymer, a dioxanone polymer, or a combination thereof. Any appropriate biodegradable material derived from biomass may be adopted as the biodegradable material derived from biomass. An example of the biodegradable material derived from biomass is an animal-derived biodegradable material. The animal-derived biodegradable material is preferably fibroin (such as a constituent material of silk), a serous membrane (such as a constituent material of catgut), spidroin (such as a constituent material of spider silk), or a combination thereof. The whole of the medical device 10 may be formed of the biodegradable material. When the device has the configuration described above, at least one portion of the medical device is degraded in a lumen of a gastrointestinal tract. As a result, the need for the removal of the used medical device by invasive measures (e.g., a surgical procedure or an endoscopic surgical procedure) can be eliminated. In addition, when an appropriate biodegradable material is selected in consideration of the durability of the device in the lumen of the gastrointestinal tract, a period for which a suppressive effect on obesity is exhibited can be easily adjusted.

Any appropriate non-biodegradable material may be adopted as the non-biodegradable material. Examples of the non-biodegradable material include a synthetic polymer, a material derived from biomass, a metal, and a combination thereof. Any appropriate synthetic polymer may be adopted as the synthetic polymer. Examples of the synthetic polymer include an olefin-based polymer (such as polyvinyl chloride, polyethylene, or polypropylene), a urethane-based polymer (such as polyurethane), silicone, an amide-based polymer (such as Nylon (trademark)), an ester-based polymer, and a combination thereof. Any appropriate material derived from biomass may be adopted as the material derived from biomass. Any appropriate metal may be adopted as the metal. An example of the metal is an iron-containing metal (such as stainless steel).

Typical examples of the material which constitutes the medical device 10 include a synthetic polymer, a metal, and a combination thereof. When the device has the configuration described above, a risk of infection during the use of the medical device can be more surely eliminated.

The medical device 10 may contain a radiopaque substance. Examples of the medical device containing the radiopaque substance include: a medical device to which a member containing the radiopaque substance is attached; a medical device formed of a material containing the radiopaque substance; a medical device coated with a material containing the radiopaque substance; and a medical device in which the radiopaque substance is embedded. Any appropriate substance may be adopted as the radiopaque substance. Examples of the radiopaque substance include barium sulfate, any appropriate metallic material having radiopacity, and any appropriate material used as a radiopaque marker in a medical device (e.g., a catheter or a stent). Examples of the metallic material having radiopacity include platinum, palladium, a platinum-iridium alloy, and a platinum-nickel alloy. Examples of the member containing the radiopaque substance include a wire and a contrast thread. The member is typically formed of fibers each containing the radiopaque substance (e.g., barium sulfate). When the medical device 10 contains the radiopaque substance, the position and movement of the medical device during the use can be easily monitored through radioscopy.

At least one portion of the medical device 10 may be coated with any appropriate material. An example of the material is a material including an antimicrobial material (e.g., fluorine). As specific products thereof, there are given, for example, "CYTOP" (manufactured by Asahi Glass Co., Ltd.), "Novec EGC-1720" and "Novec EGC-1700" (manufactured by 3M), "DEFENSA TR" (manufactured by Dainippon Ink And Chemicals, Inc.), and a combination thereof. Any appropriate method may be adopted as a method of coating the medical device 10. Examples of the method include a method involving dipping the medical device 10 in a coating material and then drying the coated device, and a method involving spraying the coating material onto the medical device 10. When the medical device 10 is coated with the material including the antimicrobial material, the adherence of a microorganism mixed in a digested content and the formation of a biofilm can be easily prevented.

A-3. Constituent Material of Cylindrical Part 3

Any appropriate material may be adopted as a material which constitutes the cylindrical part 3. An example of the material is the material which constitutes the medical device 10 described above.

The material which constitutes the cylindrical part 3 may contain a material having elasticity. An example of the material having elasticity is an elastomer. Examples of the elastomer include a rubber, a thermoplastic elastomer, and a combination thereof. When the material which constitutes the cylindrical part 3 contains the material having elasticity, the cylindrical part may easily deform in accordance with a motility of a gastrointestinal tract. As a result, the followability of the cylindrical part to a shape of an inner wall of the gastrointestinal tract is improved, and a physical stimulus given to the inner wall of the gastrointestinal tract by a digested content increases. Therefore, a preventive effect on the atrophy of the gastrointestinal mucosa is improved.

At least one portion of the cylindrical part 3 may be formed of a nonwoven fabric. Any appropriate fiber may be adopted as a fiber which constitutes the nonwoven fabric. Examples of the fiber include a fiber derived from an olefin-based polymer (e.g., a polypropylene fiber or a polyethylene fiber), a fiber derived from an ester-based polymer (e.g., a polyester fiber) and a combination thereof. When at least one portion of the cylindrical part 3 is formed of a nonwoven fabric, the permeability of the portion of the nonwoven fabric is reduced and hence the corresponding inside of a lumen of a gastrointestinal tract may be effectively protected.

At least one portion of the cylindrical part 3 is preferably formed of a fiber. Any appropriate fiber may be adopted as the fiber. An example of the fiber is a fiber formed of the material which constitutes the medical device 10. The fiber may be a biodegradable fiber or a non-biodegradable fiber. When at least one portion of the cylindrical part 3 is formed of the fiber, at least one portion of the cylindrical part can be easily of a net form. In addition, when the fiber is the biodegradable fiber (e.g., a suture thread), in the medical device indwelled in a gastrointestinal tract, the cylindrical part is gradually degraded and the degraded cylindrical part is eliminated with feces. Therefore, the treatment of obesity can be performed without any surgical removal of the indwelled cylindrical part from the gastrointestinal tract.

Any appropriate biodegradable fiber may be adopted as the biodegradable fiber. An example of the biodegradable fiber is a fiber formed of the biodegradable material which constitutes the medical device 10. Specific examples of the biodegradable fiber include PDSII (trademark), Maxon, Dexon (trademark), VICRYL (trademark), a silken thread, spider silk, catgut, VICRYL RAPIDE (trademark), MONOCRYL (trademark), and a combination thereof. The biodegradable fiber is preferably PDSII (trademark), Maxon, Dexon (trademark), VICRYL (trademark), or a combination thereof.

Any appropriate non-biodegradable fiber may be adopted as the non-biodegradable fiber. An example of the non-biodegradable fiber is a fiber formed of the non-biodegradable material which constitutes the medical device 10. Specific examples of the non-biodegradable fiber include a polyamide-based fiber, a polyolefin-based fiber, a metal fiber, and a combination thereof. An example of the polyamide-based fiber is Nylon (trademark). An example of the polyolefin-based fiber is a polypropylene fiber. An example of the metal fiber is a stainless-steel fiber.

In addition, the fiber may contain a stretched fiber. When the fiber includes the stretched fiber, the fiber does not easily elongate and hence a direction in which the cylindrical part elongates can be easily adjusted.

Any appropriate size may be adopted as an average diameter D of the fiber. The average diameter D is, for example, from 100 μm to 1 mm. When the average diameter D falls within the range, in the case where the biodegradable material is used in at least one portion of the fiber, a period for which the medical device retains its shape and a suppressive effect on the digestion and absorption is exhibited can be easily controlled. The control is performed by, for example, a method involving selecting an appropriate biodegradable fiber in consideration of the durability of the device in a lumen of a gastrointestinal tract.

The net 31 may be preferably formed of the fiber. The net 31 may be produced by any appropriate method. An example of a method of forming the net 31 is a method including a step of forming, a step of braiding (e.g., a step of knitting by stockinet), a step of weaving, a step of bonding, a step of entwining, or a combination of these steps. The method preferably includes a step of forming, a step of braiding, or a step of weaving. An example of the forming is any appropriate forming. The forming is preferably an extrusion. When at least one portion of the net 31 is produced by a method including a step of forming, a direction in which the cylindrical part elongates can be easily adjusted. When at least one portion of the net 31 is a portion produced by a method including a step of braiding or a step of weaving, the number of options of a material which constitutes the net increases. In addition, the strength of the net produced by the method described above is improved. The step of bonding and the step of entwining may be performed by any appropriate treatments. Examples of the treatment include a physical treatment (e.g., heat treatment and mechanical treatment) and chemical treatment.

A-4. Constituent Material of Attachment Part

Any appropriate material may be adopted as a material which constitutes the attachment part 2. An example of the material is a material which constitutes the medical device 10 described above.

A-5. Variation of Medical Device

Figure 2:
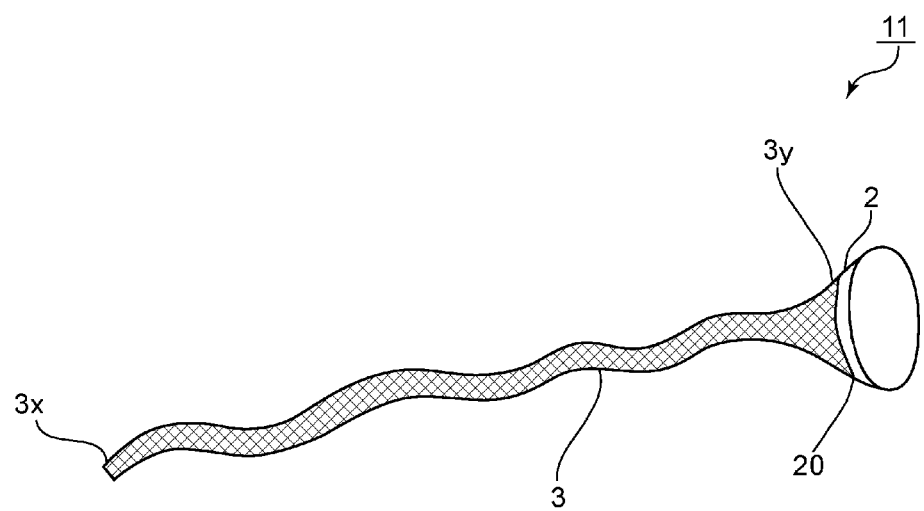
FIG. 2 is a schematic view of a medical device according to another embodiment of the present invention.

FIG. 2 is a schematic view of a medical device 11 according to another embodiment of the present invention. In the illustrated example, the attachment part 2 and the cylindrical part 3, which are joined, are materials different from each other. The attachment part 2 and the cylindrical part 3 are joined at a boundary 20 between the attachment part 2 and the end 3y of the cylindrical part 3. Any appropriate means may be adopted as the joint means. Examples of the joint means include a thread (e.g., a suture thread), a stapler, an adhesive, a hook, and a combination thereof.

Figure 3:
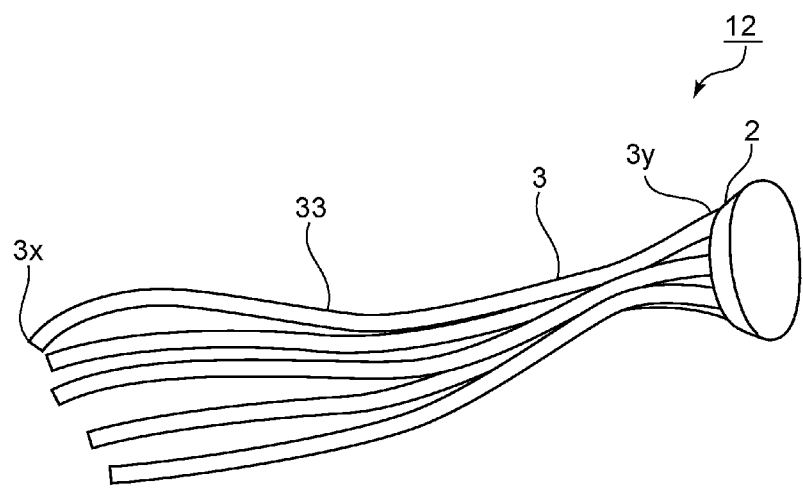
FIG. 3 is a schematic view of a medical device according to still another embodiment of the present invention.

FIG. 3 is a schematic view of a medical device 12 according to still another embodiment of the present invention. In the illustrated example, the shape of the cylindrical part 3 is of a strip form. Any appropriate strip may be adopted as a strip 33 defined by a shape of the strip form.

Any rate may be adopted as a rate of a length of the strip 33 to a length of the whole of the cylindrical part 3. The rate is, for example, from 80% to 100%. When the rate falls within the range, the atrophy of a gastrointestinal mucosa and a dumping syndrome can be more effectively prevented. In the illustrated example, the strip 33 extends from the end 3x toward the end 3y of the cylindrical part 3.

Figure 4:
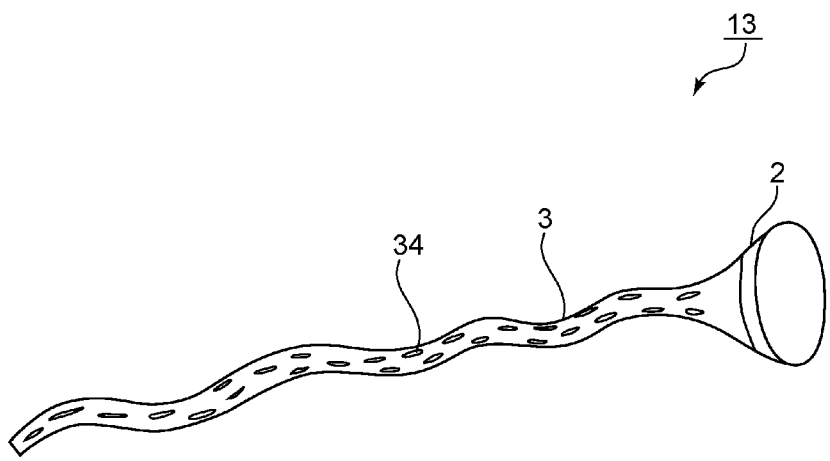
FIG. 4 is a schematic view of a medical device according to yet still another embodiment of the present invention.

FIG. 4 is a schematic view of a medical device 13 according to yet still another embodiment of the present invention. In the illustrated example, the cylindrical part 3 has a slit form.

Any appropriate slit may be adopted as a slit 34 defined by a shape of the slit form.

Any appropriate direction may be adopted as a direction of the slit 34. In the illustrated example, the longitudinal direction of the slit 34 is substantially parallel to the longitudinal direction of the cylindrical part 3.

Any appropriate aperture ratio may be adopted as an aperture ratio of the slits 34. The aperture ratio of the slits 34 is, for example, from 40% to 70%. When the aperture ratio falls within the range, the atrophy of a gastrointestinal mucosa and a dumping syndrome are effectively prevented, and a sufficient suppressive effect on the digestion and absorption can be achieved by the medical device.

Figure 5:
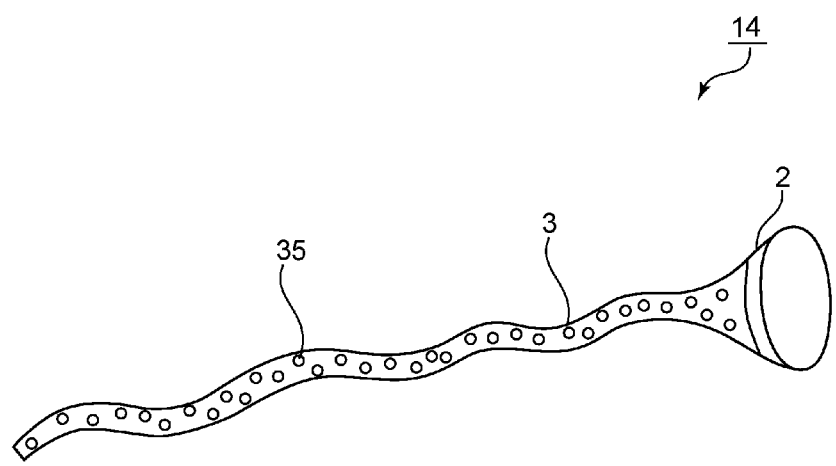
FIG. 5 is a schematic view of a medical device according to even yet still another embodiment of the present invention.

FIG. 5 is a schematic view of a medical device 14 according to even yet still another embodiment of the present invention. In the illustrated example, the cylindrical part 3 has a perforated form.

Any appropriate hole may be adopted as a hole 35 defined by a shape of the perforated form. The hole 35 may have any appropriate shape. Examples of the shape include a substantially multiangular shape, a substantially elliptical shape (e.g., a substantially circular shape), and a combination thereof. In the illustrated example, the hole 35 has a substantially circular shape.

Any appropriate aperture ratio may be adopted as an aperture ratio of the holes 35. The aperture ratio of the holes 35 is, for example, from 40% to 70%. When the aperture ratio falls within the range, the atrophy of a gastrointestinal mucosa and a dumping syndrome are effectively prevented, and a sufficient suppressive effect on the digestion and absorption can be achieved by the medical device.

Figure 6:
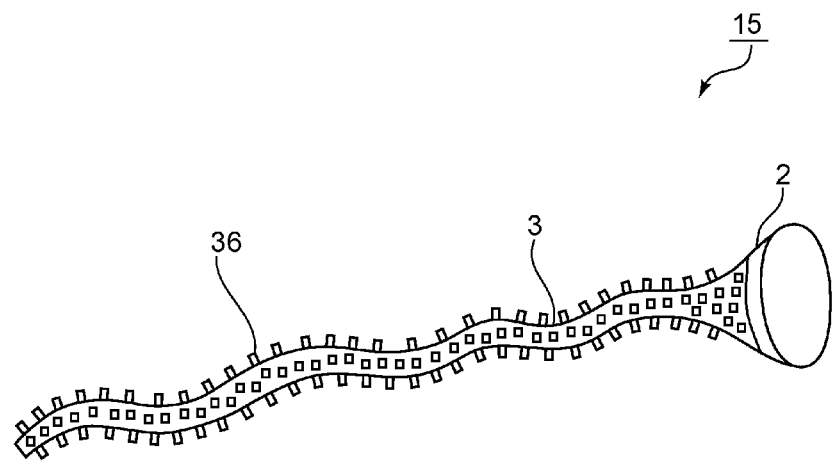
FIG. 6 is a schematic view of a medical device according to even yet still another embodiment of the present invention.

FIG. 6 is a schematic view of a medical device 15 according to even yet still another embodiment of the present invention. In the illustrated example, the cylindrical part 3 has an irregular form. When at least one portion of the cylindrical part 3 has an irregular form, the cylindrical part can apply a more intense physical stimulus to an inner wall of a gastrointestinal tract, and hence a preventive effect on the atrophy of the gastrointestinal mucosa is improved. In addition, the cylindrical part is hardly twisted in the gastrointestinal tract, and hence an occlusion of the gastrointestinal tract can be easily prevented.

Any appropriate convex part may be adopted as a convex part 36 forming the irregular form described above. Any appropriate height may be adopted as a height of the convex part 36. The height of the convex part 36 is, for example, from 1 mm to 5 cm. When the height of the convex part 36 is a certain height or more, a preventive effect on the atrophy of a gastrointestinal mucosa and an occlusion of a gastrointestinal tract is further improved.

Figure 7:
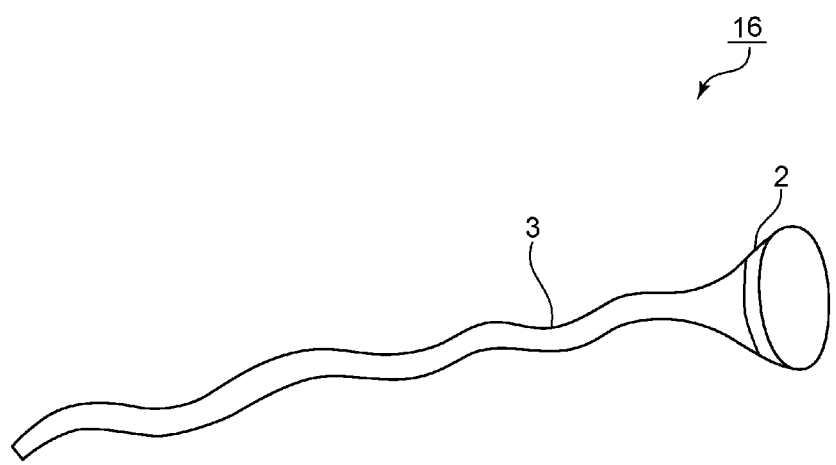
FIG. 7 is a schematic view of a medical device according to even yet still another embodiment of the present invention.

FIG. 7 is a schematic view of a medical device 16 according to even yet still another embodiment of the present invention. In the illustrated example, the cylindrical part 3 has a membrane form.

Any appropriate membrane may be adopted as a membrane forming a shape of the membrane form. Any appropriate material may be adopted as a material which constitutes the membrane. An example of the material which constitutes the membrane is the material which constitutes the medical device 10. The material is preferably a metal. A specific example of the membrane is a metal foil.

In embodiments illustrated in FIG. 2 to FIG. 7, the attachment part 2 and the cylindrical part 3 are members different from each other, but, of course, may be integrally formed. In addition, the embodiments described above may be appropriately combined with each other, or may be combined with a configuration well known in the art.

B. Application of Medical Device

The medical device may be used in any appropriate applications in addition to obesity treatment. Examples of the applications include drug administration, the protection of an inside of a lumen of a gastrointestinal tract, and a combination thereof.

As a medical device used in a drug administration, there is given, for example, a medical device containing a drug. Examples of the medical device containing a drug include a medical device which is formed of a material mixed with a drug, and a medical device coated with a drug. When the medical device containing a drug is arranged in a lumen of a gastrointestinal tract, the device can control the body weight of a subject and also sustain the efficacy of the drug which has been not absorbed in the gastrointestinal tract. This is because the drug not absorbed in the gastrointestinal tract, which exhibits its efficacy in proportion to an amount of oral intake, can be administered in a large amount through the medical device without oral intake. In addition, when a drug is released from a specific portion of the medical device, the drug (e.g., a therapeutic agent for gastric ulcer or a therapeutic agent for ulcerative colitis) can be directly administrated to a local portion of the gastrointestinal tract.

Any appropriate drug may be adopted as the drug. The drug is preferably a drug which exhibits its function in a gastrointestinal tract. More specific examples of the drug include a therapeutic agent for renal failure (such as activated charcoal (such as Kremezin)), a therapeutic agent for hyperkalemia (such as an ion-exchange resin (such as sodium polystyrene sulfonate)), a therapeutic agent for hypercholesterolemia (such as an anion-exchange resin (such as colestimide)), a therapeutic agent for ulcerative colitis, a therapeutic agent for gastric ulcer, a mucoprotective agent (such as Marzulene-S, Monilac, or a combination thereof), a diet prompter (such as mucin, a fiber, bifidobacteria, an alimentary bolus-solidifying action substance, or a combination thereof), and a combination thereof. When a diet promotor is used as the drug, a diet effect can be promoted.

As a medical device used for the protection of the inside of a lumen of a gastrointestinal tract, there is given, for example, a medical device in which at least one portion of the cylindrical part 3 has reduced permeability. At least one portion of the portion having reduced permeability of the cylindrical part 3 may be formed of a nonwoven fabric. As a position of the portion having reduced permeability of the cylindrical part 3, there is given, for example, includes a position corresponding to a site in need of protection of the inside of the lumen of the gastrointestinal tract. An example of the site in need of protection is a lesion in the lumen of the gastrointestinal tract (e.g., a site of cancer and/or ulcer of the gastrointestinal tract). When the device has the configuration described above, the inside of the lumen of the gastrointestinal tract can be effectively protected.

C. Arrangement State of Medical Device in Lumen of Gastrointestinal Tract

Figure 8:
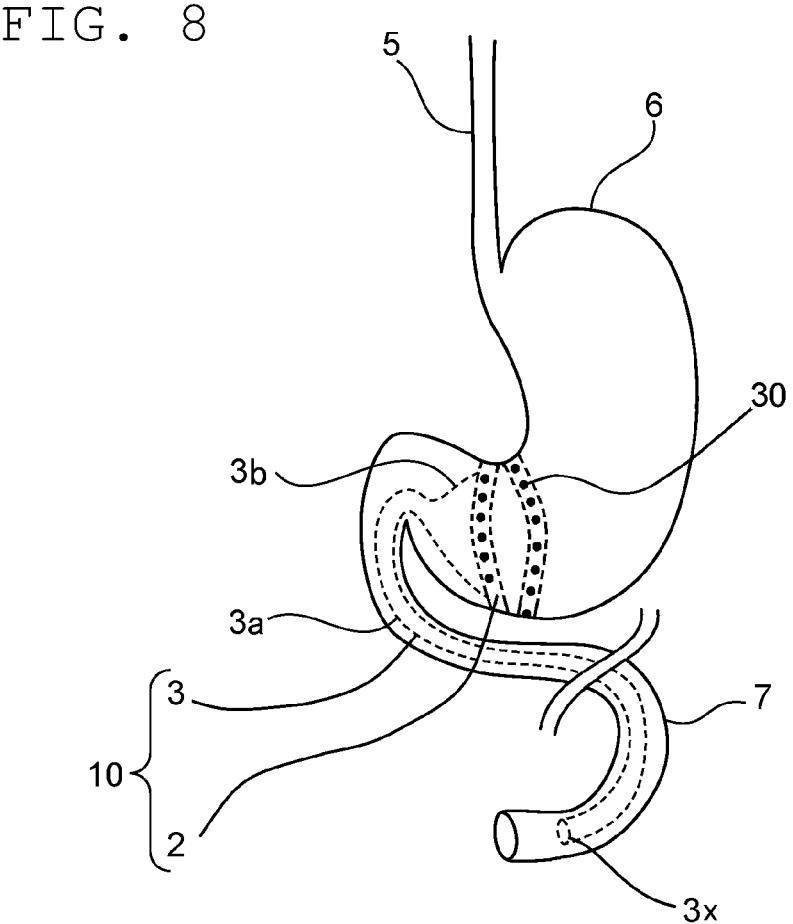
FIG. 8 is a schematic view for illustrating one example of a state in which a medical device according to one embodiment of the present invention is arranged in a lumen of a gastrointestinal tract.

The medical device 10 may be arranged in a lumen of a gastrointestinal tract in any appropriate state. FIG. 8 is a schematic view for illustrating one example of a state in which the medical device 10 according to one embodiment of the present invention is arranged in the lumen of the gastrointestinal tract.

Typically, when the attachment part 2 is attached to at least one portion of an inner wall of the gastrointestinal tract, the medical device 10 is arranged in the lumen of the gastrointestinal tract. In the illustrated example, when the attachment part 2 is attached to a stomach 6, the medical device 10 is arranged from the stomach 6 along an intestinal tract 7. Herein, the intestinal tract is considered as a concept including a duodenum.

The attachment part 2 is typically attached along the entire circumference of the inner wall of the gastrointestinal tract. In the illustrated example, the attachment part 2 is attached over the entire circumference of an inner wall of the stomach 6.

In the illustrated example, the attachment part 2 is attached along the inner wall of the gastrointestinal tract through attachment means 30. Any appropriate means may be adopted as the attachment means 30. Examples of the attachment means 30 include a thread (e.g., a suture thread), a stapler, a clip, and a combination thereof.

Any appropriate gastrointestinal tract may be adopted as a gastrointestinal tract to which the attachment part 2 is attached. Examples of the gastrointestinal tract include an esophagus, a stomach, and an intestinal tract. The gastrointestinal tract described above is preferably the stomach (e.g., a pyloric end of the stomach, a gastric cardia, or an adjacent portion thereof). In the illustrated example, the attachment part 2 is attached to the pyloric end of the stomach 6. When an attachment position of the attachment part 2 is selected, an absorption rate by the gastrointestinal tract may be easily adjusted. This is because of the following reason. Through the attachment position, an expansion state of the gastrointestinal tract may be controlled, and hence a feeling of fullness and a motility of the gastrointestinal tract change, resulting in changes of the digestion and degradation of a food.

The cylindrical part 3 is typically arranged downstream the gastrointestinal tract to which the attachment part 2 is attached. The cylindrical part 3 is preferably arranged along at least one portion of the stomach 6 and the intestinal tract 7, or at least one portion of the intestinal tract 7. In the illustrated example, the cylindrical part 3 is arranged from the pyloric end of the stomach 6 along the intestinal tract 7.

In the intestinal tract 7, any appropriate rate may be adopted as a rate of a length which the cylindrical part 3 accounts for. The rate is, for example, from 30% to 80%.

The fixed region 3a of the cylindrical part 3 may be arranged in any appropriate position. In the illustrated example, the fixed region 3a is arranged along the intestinal tract 7.

The enlargement region 3b of the cylindrical part 3 may be arranged in any appropriate position. In the illustrated example, the enlargement region 3b is arranged along the pyloric end of the stomach 6. When the enlargement region 3b is arranged along a specific gastrointestinal tract (e.g., the stomach 6), an expansion state of the gastrointestinal tract can be adjusted during the use of the medical device, and hence effects on a feeling of fullness, and a motility of a gastrointestinal tract, of a subject can be easily controlled. As a result, the digestion and degradation of a food, and an absorption rate of a gastrointestinal tract lied downstream the whole of the gastrointestinal tract (e.g., the intestinal tract 7) are controlled, and hence a suppressive effect on the digestion and absorption can be easily adjusted.

D. Method of Arranging Medical Device in Lumen of Gastrointestinal Tract

Figure 9:
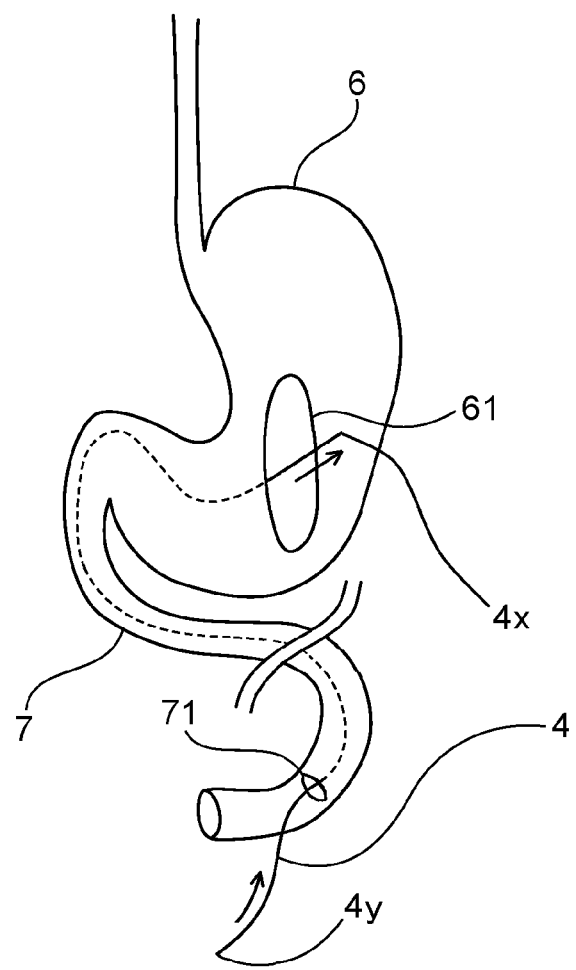
FIG. 9 is a schematic view for illustrating one example of a method of arranging a medical device according to one embodiment of the present invention in a lumen of a gastrointestinal tract.
Figure 10:
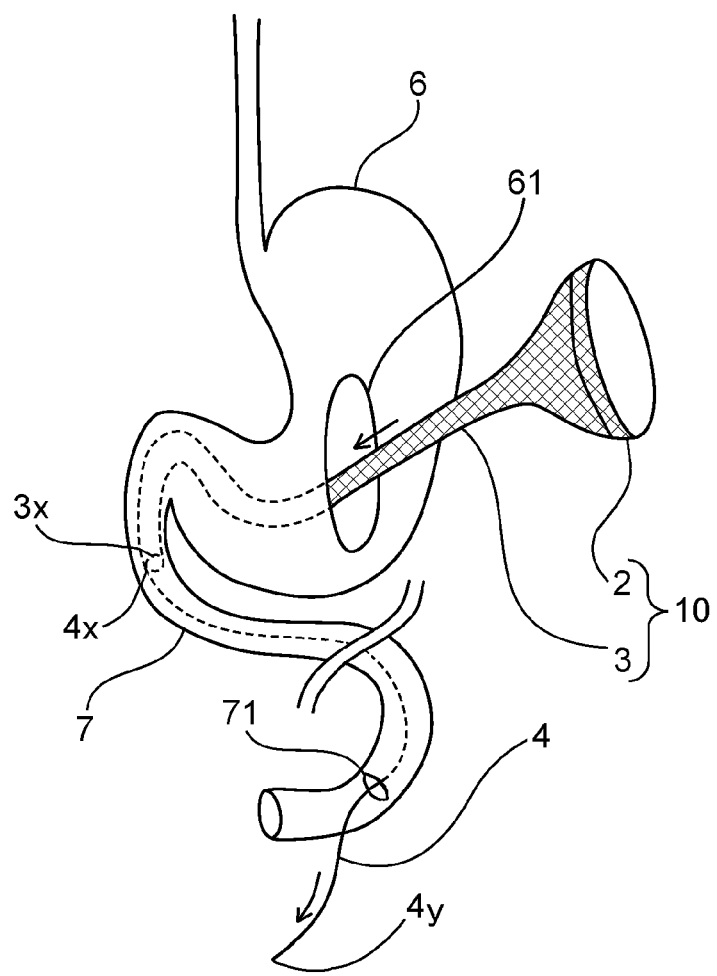
FIG. 10 is a schematic view for illustrating the one example of the method of arranging the medical device according to the one embodiment of the present invention in the lumen of the gastrointestinal tract.
Figure 11:
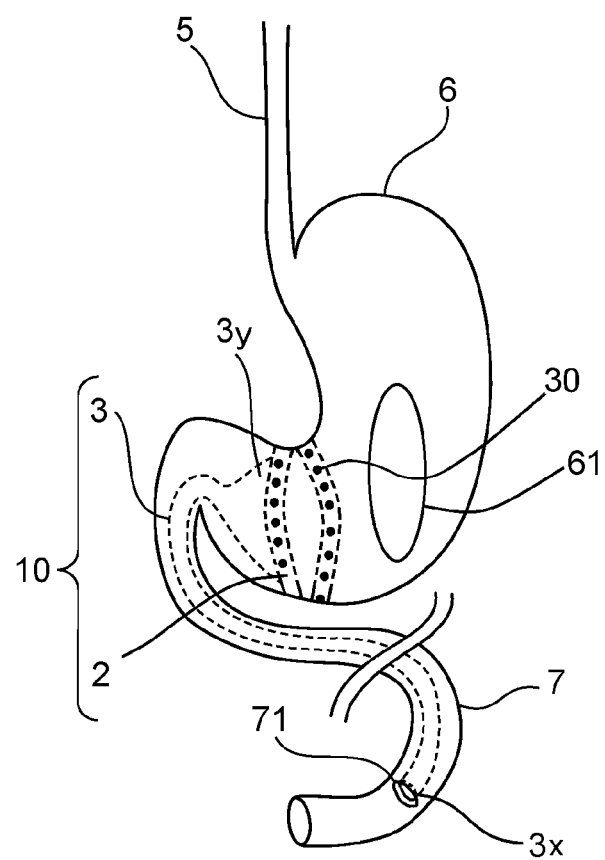
FIG. 11 is a schematic view for illustrating the one example of the method of arranging the medical device according to the one embodiment of the present invention in the lumen of the gastrointestinal tract.

FIG. 9 to FIG. 11 are schematic views for illustrating one example of a method of arranging the medical device 10 according to one embodiment of the present invention in a lumen of a gastrointestinal tract.

In a subject under laparotomy, an intestinal tract perforation part 71 is formed by surgically perforating the intestinal tract 7. A position on which the intestinal tract perforation part 71 is formed is a position on which the end 3x of the cylindrical part 3 is to be arranged. In addition, a stomach incision part 61 is formed by surgically incising the stomach 6 at the anterior side. To the intestinal tract perforation part 71, a blunt needle with a thread 4 is inserted, and as shown as the arrows in FIG. 9, the blunt needle with a thread 4 is fed in a direction from the intestinal tract perforation part 71 toward the stomach incision part 61 (i.e., in a retrogressive fashion). When the blunt needle with a thread 4 is fed, one end 4x of the blunt needle with a thread 4 passes through the stomach incision part 61 (FIG. 9). At this stage, another end 4y of the blunt needle with a thread 4 is positioned outside the intestinal tract perforation part 71 (FIG. 9).

Then, the end 4x of the blunt needle with a thread 4 is bonded to the end 3x of the cylindrical part 3 and the end 4y of the blunt needle with a thread 4 is pulled, so that the medical device 10 and the blunt needle with a thread 4 are, as shown as the arrows in FIG. 10, fed in a direction from the stomach incision part 61 toward the intestinal tract perforation part 71 (i.e., in an anterograde fashion). When the medical device 10 and the blunt needle with a thread 4 are fed, the end 3x of the cylindrical part 3 reaches the intestinal tract perforation part 71, and the attachment part 2 reaches the pyloric end of the stomach 6 (not shown). At this stage, the cylindrical part 3 is separated from the blunt needle with a thread 4, and then the end 3x of the cylindrical part 3 is arranged on the position on which the intestinal tract perforation part 71 is formed in the intestinal tract 7 (FIG. 11). The attachment part 2 is fixed with a thread and/or a stapler along the entire circumference of the inner wall of the pyloric end of the stomach 6 (i.e., in an entire circumferential fashion) (FIG. 11). The stomach incision part 61 and the intestinal tract perforation part 71 are sutured to close the abdomen. Through the above-described method, the medical device 10 is arranged in the lumen of the gastrointestinal tract in the mode illustrated in FIG. 8.

Figure 12:
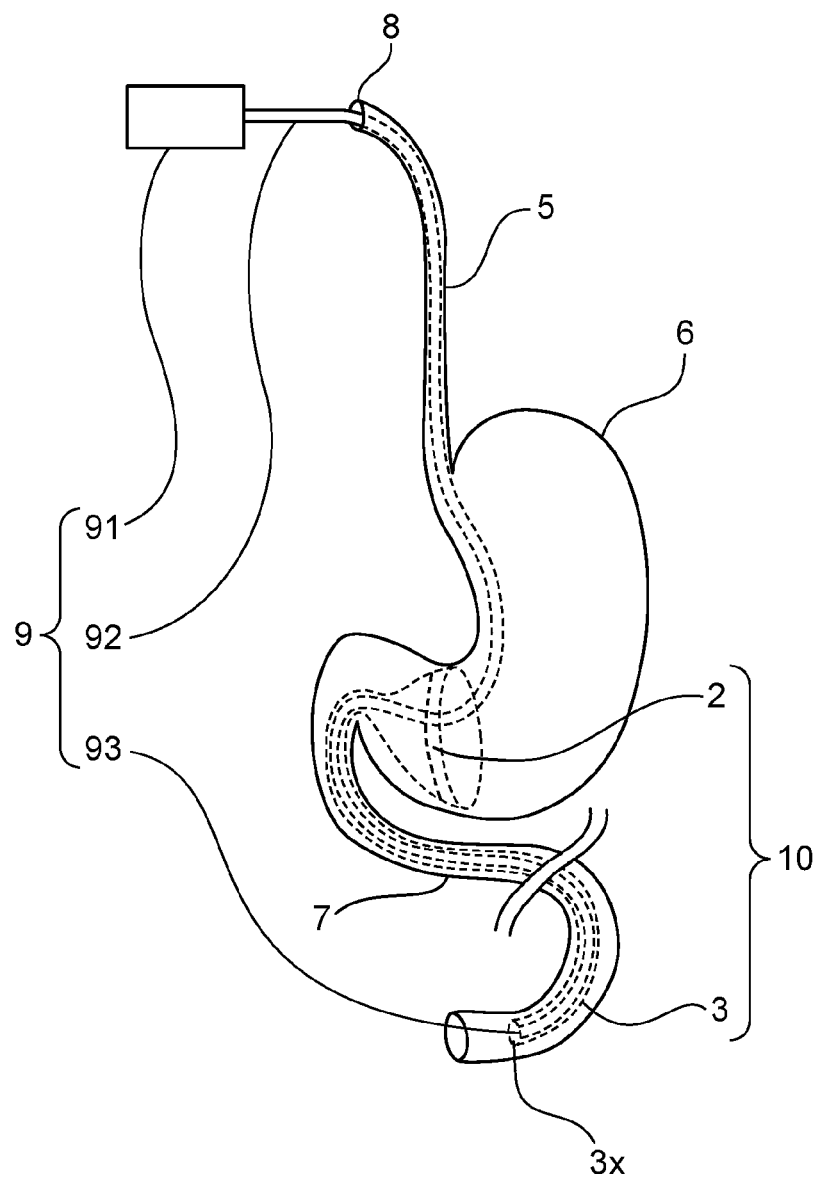
FIG. 12 is a schematic view for illustrating one example of a method of arranging a medical device according to one embodiment of the present invention in a lumen of a gastrointestinal tract.

FIG. 12 is a schematic view for illustrating one example of a method of arranging the medical device 10 according to one embodiment of the present invention in a lumen of a gastrointestinal tract.

An endoscope 9 is set up. The endoscope 9 includes an operation part 91, a tube part 92, and a foreign-body forceps 93 in the stated order from an operator's side. To the inside of the cylindrical part 3 of the medical device 10, the foreign-body forceps 93 is inserted, followed by the insertion of the endoscope 9, and then the end 3x of the cylindrical part 3 is held by the foreign-body forceps 93 (not shown). Through the operation part 91, the end 3x of the medical device 10 and the foreign-body forceps 93 are inserted, followed by the insertion of the medical device 10 and the endoscope 9 from an oral cavity 8 (FIG. 12). The end 3x and the foreign-body forceps 93 are passed through the stomach 6, and are inserted into the intestinal tract 7 to feed the attachment part 2 to the pyloric end of the stomach 6 (FIG. 12). At this stage, the holding of the end 3x by the foreign-body forceps 93 is released, and then only the endoscope 9 is pulled into the inside of the stomach 6 (not shown). The attachment part 2 is fixed on at least 8 points along the entire circumference of the inner wall of the pyloric end of the stomach 6 using hemostatic clips. Through the above-mentioned process, the medical device 10 is arranged in the lumen of the gastrointestinal tract in the mode illustrated in FIG. 8.

EXAMPLES

The present invention is specifically described below by way of Examples, but the present invention is not limited to these Examples.

The medical device 10 according to one embodiment of the present invention was arranged in a lumen of a gastrointestinal tract in an animal, and changes of the body weight were measured in order that a suppressive effect on the digestion and absorption, and a preventive effect on the atrophy of the gastrointestinal mucosa, of the medical device were examined. A Gastro Jejunal Inner Lumen membrane Windsock shaped medical device with both opened ends was used as the medical device 10. The medical device is hereinafter referred to as a GJIMW device. A specific method for examination is as described below.

(Management of Animal)

Seven male Landrace large White Duroc pigs (LWD, purchased from Seiko Tikusan, Ltd.) at 4 weeks of age having an average body weight of 7.31 kg were used as subject animals in this experiment. In order to estimate an effect on the medical device on physiological gains of the body weight, young animals in growth period were used. The animals were each raised in an individual cage under a constant temperature and constant light-dark cycle. The animals took a feed (manufactured by Nosan Corporation) and water ad libitum. The cages were cleaned 7 times a week and an additional feed was supplied once a day. The feed was given at a certain amount everyday in conformity to Japanese Feeding Standard for Swine (Japan Livestock Industry Association, 2005).

(Operation of Animal)

To each of the animals, 0.03 mg/kg of medetomidine (trade name "DOMITOR" (trademark), manufactured by Orion Corporation), 0.25 mg/kg of midazolam (trade name "DORMICUM" (trademark), manufactured by Astellas Pharma Inc.), and 0.15 mg/kg of butorphanol (trade name "VETORPHALE" (trademark), manufactured by Meiji Seika Pharma Co., Ltd.) were intramuscularly injected as sedative agents. The intravenous line was established and then 1 mg/kg to 2 mg/kg of propofol (trade name "MYLAN", manufactured by Intervet K.K. was given as an anesthetic agent to the animal. Subsequently, the animal was subjected to tracheal cannulation and took a breath at a pace controlled by a veterinary anesthesiologist. As required, the controlled breathing was changed to spontaneous breathing. Anesthesia was maintained with 0.8% to 1.6% isoflurane (trade name "ISOFLU", manufactured by DS Pharma Animal Health Co., Ltd.) at end-expiration until the completion of the operation. To prevent an infection, on pre-operation and for 5 days after operation, 20 mg/kg of cefazolin (trade name "Cefamezin", manufactured by Astellas Pharma Inc.) was intravenously given to the animal twice a day. The operation was performed on the animal by the method described in the section D with reference to FIG. 9 to FIG. 11, and a GJIMW device was arranged in a lumen of a gastrointestinal tract of the animal. In the operation, a feeding catheter (trade name "New Enteral feeding tube", manufactured by Covidien AG) was used as a blunt needle with a thread. One end of the GJIMW device was fixed to the entire layer of the inner wall in the small intestine by sewing with a biodegradable suture thread. Another end of the GJIMW device (the end of the jejunum side) was also fixed with two biodegradable suture threads. The stomach incision part and the intestinal tract perforation part were sutured, and then the abdominal closure was performed, followed by washing with physiological saline. After 15 hours from the operation, the animals were able to take a feed (manufactured by Nosan Corporation) and water ad libitum.

Example 1

Figure 13:
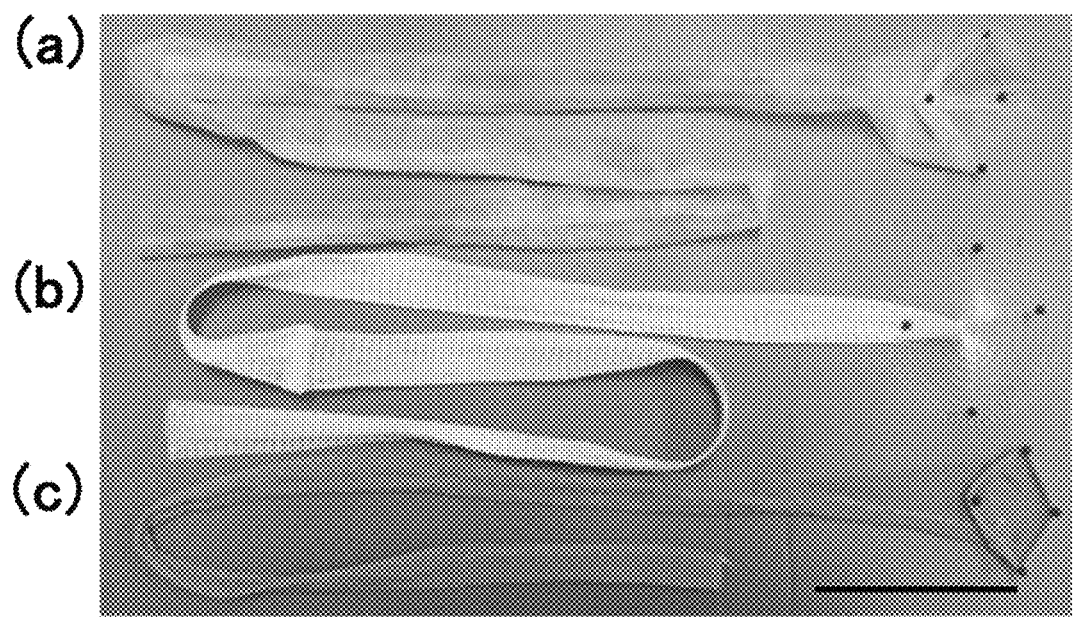
FIG. 13 is a photograph of the medical devices which are used in Example 1, Example 2, and Example 4.
Figure 14:
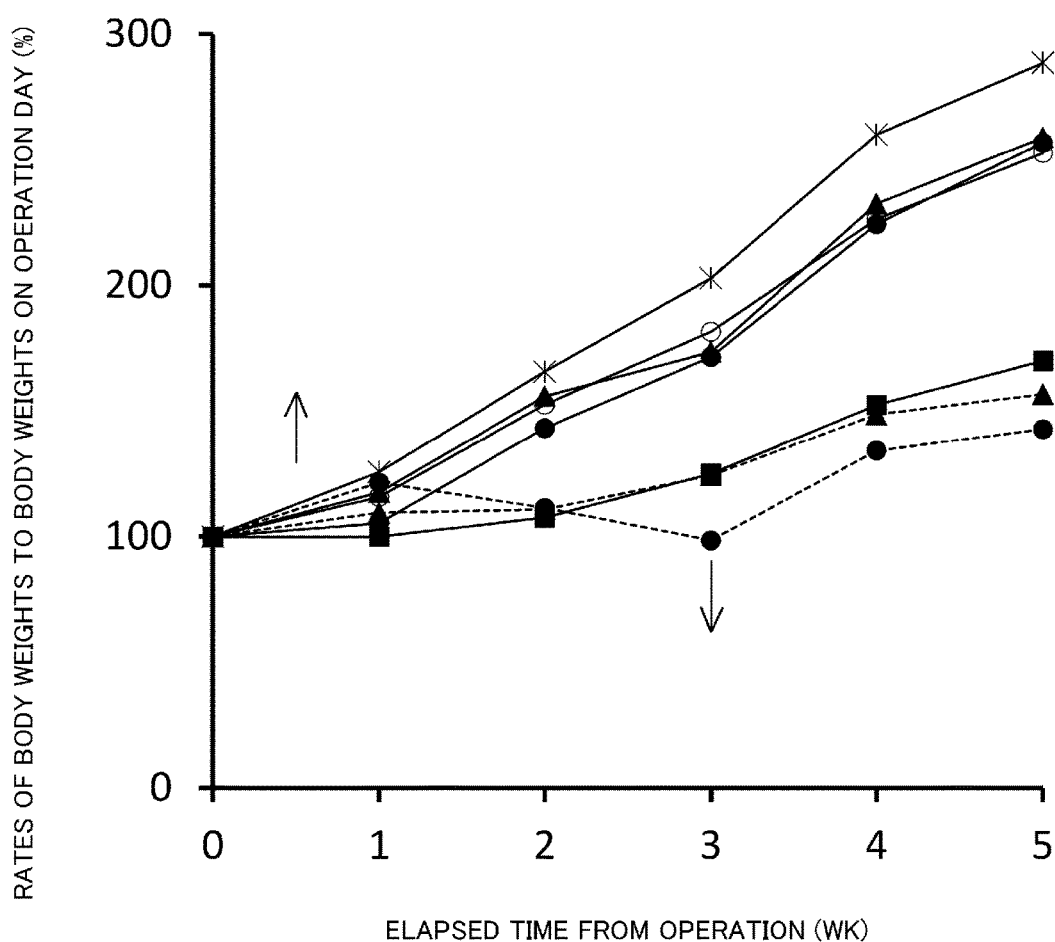
FIG. 14 is a graph for showing measurement results of body weights in Examples 1 to 5 and Comparative Examples 1 and 2.

A nonwoven fabric GJIMW device (Nonwoven, 125 cm, made of polypropylene, manufactured by Dio Chemicals, Ltd.) was used as a medical device. The GJIMW device had a constant width of 2 cm at the small intestine side. The GJIMW device is shown as (a) in the top of the photograph in FIG. 13. A scale bar shown in FIG. 13 represents a length of 10 cm. Body weights of the animal were measured every week after the operation. The results are shown in the graph of FIG. 14. In addition, on pre-operation and 5 weeks after the operation, hematological examinations were performed. The results are shown in Table 1. After the measurement of body weights and the hematological examinations, 64.8 mg/kg of pentobarbital sodium (trade name "SOMNOPENTYL", manufactured by Kyoritsuseiyaku Corporation) was intravenously injected to the animal under ordinary anesthesia to sacrifice the animal.

Example 2

The same experiment as that in Example 1 was performed except that a net-formed GJIMW device (Short fabric net, 45 cm, made of polyethylene, manufactured by Morishita Inc.) was used.

Example 3

The same experiment as that in Example 1 was performed except that a net-formed GJIMW device (Long fabric net, 115 cm, made of polyethylene, manufactured by Morishita Inc.) was used. The GJIMW device is shown as (b) in the middle of the photograph in FIG. 13.

Example 4

The same experiment as that in Example 1 was performed except that a stocking (Short nylon stocking, 35 cm, made of nylon, manufactured by Atsugi Co., Ltd.) was used as a GJIMW device.

Example 5

The same experiment as that in Example 1 was performed except that a stocking (Long nylon stocking, 109 cm, made of nylon, manufactured by Atsugi Co., Ltd.) was used as a GJIMW device. The GJIMW device is shown as (c) in the bottom of the photograph in FIG. 13.

Comparative Example 1

The same experiment as that in Example 1 was performed except that an operation was not performed and a GJIMW device was not arranged in a lumen of a gastrointestinal tract in the animal (Control).

Comparative Example 2

The same experiment as that in Example 1 was performed except that stomach incision and intestinal tract perforation were performed, but a GJIMW device was not arranged in a lumen of a gastrointestinal tract in the animal and the abdominal closure was performed (Sham-operated).

TABLE 1

|  |  | Total protein g/dl | Alb g/dl | Total cholesterol mg/dl | TG mg/dl | HDL mg/dl | LDL mg/dl |
|---|---|---|---|---|---|---|---|
| Standard value (Normal range) |  | 5.8-9.1 | 3.2-4.8 | 66-158 | <102 |  |  |
| Comparative Control | Pre-operation | 4.8 | 3.3 | 109 | 51 | 49.6 | 48 |
| Example 1 | 5 weeks | 4.7 | 3.6 | 75 | 45 | 34.9 | 30 |

TABLE 1-continued

|  |  |  | Total protein g/dl | Alb g/dl | Total cholesterol mg/dl | TG mg/dl | HDL mg/dl | LDL mg/dl |
|---|---|---|---|---|---|---|---|---|
| Comparative Example 2 | Sham-operated | Pre-operation | 5 | 3.6 | 124 | 66 | 56.4 | 55 |
|  |  | 5 weeks | 4.8 | 4.1 | 69 | 19 | 29.8 | 30 |
| Example 1 | Nonwoven | Pre-operation | 4.5 | 3 | 150 | 27 | 42.8 | 96 |
|  |  | 5 weeks | 5.2 | 3.3 | 116 | 43 | 44.9 | 60 |
| Example 2 | Short fabric net | Pre-operation | 4.3 | 3.2 | 79 | 23 | 42.5 | 28 |
|  |  | 5 weeks | 4.9 | 3.9 | 73 | 26 | 32.6 | 30 |
| Example 3 | Long fabric net | Pre-operation | 5.2 | 3.7 | 133 | 74 | 45 | 78 |
|  |  | 5 weeks | 5.1 | 3.4 | 95 | 73 | 42.3 | 43 |
| Example 4 | Short nylon stocking | Pre-operation | 4.4 | 3.1 | 91 | 27 | 49.9 | 36 |
|  |  | 5 weeks | 4.9 | 3.4 | 68 | 16 | 29.7 | 29 |
| Example 5 | Long nylon stocking | Pre-operation | 4.9 | 3.3 | 147 | 85 | 56.3 | 76 |
|  |  | 5 weeks | 5.5 | 4.1 | 114 | 118 | 56.2 | 44 |

In Table 1, the results obtained as described below are shown: for the animals used in Examples 1 to 5 and Comparative Examples 1 and 2, hematological examinations were performed at pre-operation and 5 weeks after the operation to measure levels of total protein, albumin (Alb), total cholesterol, triacylglycerol (TG), HDL cholesterol (HDL), and LDL cholesterol (LDL). As shown in Table 1, there was found no significant difference between the animals used in Examples 1 to 5 and the animals used in Comparative Examples 1 and 2 in terms of the results of the hematological examinations. Thus, it was considered that those animals had no difference in general health conditions.

FIG. 14 is a graph for showing the measurement results of bodyweights of the animals in Examples 1 to 5 and Comparative Examples 1 and 2. In the graph, the vertical axis represents rates of body weights on the measurement day to body weights on the operation day each of which is defined as 100%, and the horizontal axis represents the time that has elapsed from the operation by week. As shown in FIG. 14, in Example 1 (Nonwoven) and Example 3 (Long fabric net), the body weight gains were suppressed compared to Comparative Examples 1 and 2. Specifically, in Comparative Examples 1 and 2, the body weights on the operation day were 7.0 kg and 7.6 kg, respectively, and the body weights on 5th week after the operation were 19.2 kg and 20.2 kg, respectively. The body weights increased nearly three times from the operation day to 5th week after the operation. Meanwhile, in Examples 1 and 3, the body weights of the animals on the operation day were 8.0 kg and 7.4 kg, respectively, and the body weights on 5th week after the operation were 11.6 kg and 13.36 kg, respectively. The body weights increased about 1.7 times from the operation day to 5th week after the operation (about 60% of the body weights of the animals in Comparative Examples 1 and 2). Therefore, it was indicated that those GJIMW devices suppressed the digestion and absorption. In addition, in Example 5 (Long nylon stocking), the body weight decreased from 1st week to 3rd week after the operation, and the GJIMW device was excreted on 3rd week after the operation (the point illustrated with the downward arrow described in FIG. 14). As a result, the body weight gain of the animal in Example 5 was comparable to that of the animal in Comparative Example 2 from 3rd week to 5th week after the operation. Specifically, in Comparative Example 2, the body weight increased about 1.4 times from 3rd week to 5th week after the operation, and in Example 5, the body weight increased about 1.5 times in the same period. That is, it was found that even an animal with a GJIMW device, when the GJIMW device was removed off, performed the digestion and absorption to the same extent as the ordinary level. If atrophy of the gastrointestinal mucosa was caused by using the GJIMW device, it is conceivable that the body weight gain comparable to that in Comparative Example 2 would not occur. This is because digestion and adsorption efficiency would be deteriorated by the atrophy. Accordingly, it was suggested that when a GJIMW device was used, the atrophy of the gastrointestinal mucosa was prevented. In each of Example 2 (Short fabric net) and Example 4 (Short nylon stocking), the GJIMW device did not normally work, and a body weight gain similar to those of Comparative Examples 1 and 2 was recognized. Specifically, in Example 2, the GJIMW device flowed back from the duodenum to the stomach, and in Example 4, the GJIMW device flowed out from the antrum of the stomach and was excreted. The flow back and the flow out were each observed within 1 week after the operation (the point illustrated with the upward arrow described in FIG. 14).

Example 6

The animal in Example 1, which was sacrificed, was used to prepare pathological specimens of the stomach and the intestine according to the ordinary method. The sites used for the preparation of the pathological specimens were, as indicated below, a stomach non-lining part A, a stomach lining part B, an intestinal tract lining part C, and an intestinal tract non-lining part D. The pathological specimens were observed with a microscope (manufactured by Olympus Corporation, model number "BX51"), and photographs were taken at 40-fold magnification. Photographs for showing observational results of the pathological specimens of the stomach non-lining part A, the stomach lining part B, the intestinal tract lining part C, and the intestinal tract non-lining part D were shown in FIG. 16(A) to FIG. 16(D), respectively.

(Stomach Non-Lining Part A)

Stomach wall near the attachment part 2 of the medical device 10 on the esophagus 5 side That is, stomach wall which has not been lined by the medical device 10

Figure 15:
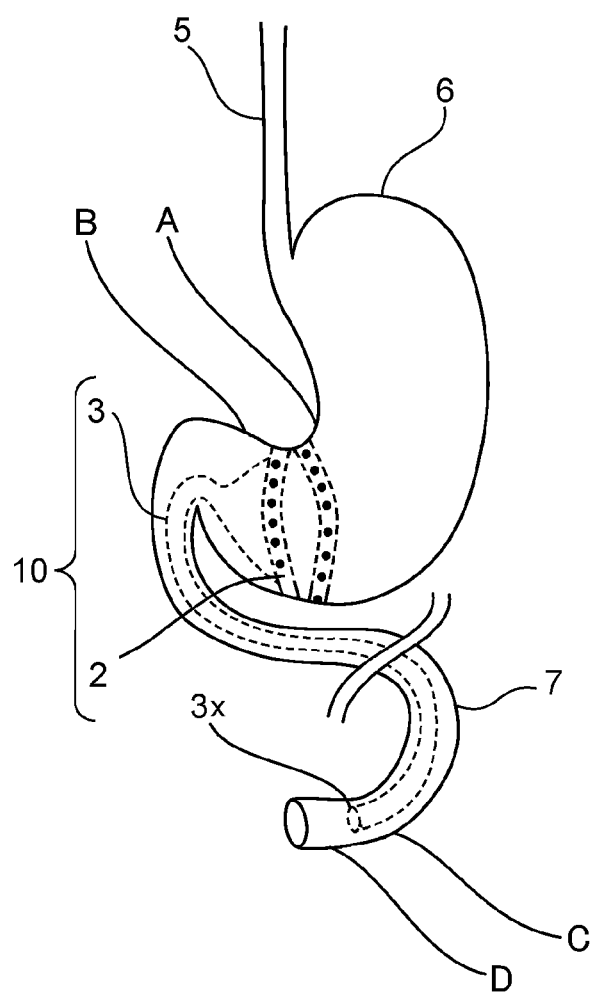
FIG. 15 is a schematic view for illustrating sites which are used to prepare pathological specimens in Examples 6 to 8.

(Site Shown as A in FIG. 15)

(Stomach Lining Part B)

Stomach wall near the attachment part 2 of the medical device 10 on the intestinal tract 7 side That is, stomach wall which has been lined by the medical device (Site Shown as B in FIG. 15)

(Intestinal Tract Lining Part C)

Intestinal tract wall near the end 3x of the medical device 10 on the stomach 6 side That is, intestinal tract wall which has been lined by the medical device 10

(Site Shown as C in FIG. 15)

(Intestinal Tract Non-Lining Part D)

Intestinal tract wall near the end 3x of the medical device 10 on the opposite side to the stomach 6

That is, intestinal tract wall which has not been lined by the medical device 10

(Site Shown as D in FIG. 15)

Figure 16A:
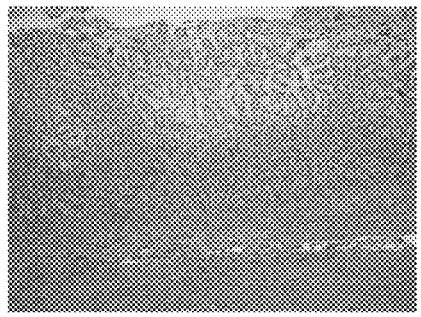
FIG. 16(A), FIG. 16(B), FIG. 16(C), and FIG. 16(D) are photographs for showing observational results of the pathological specimens in Example 6.
Figure 16D:
Figure 16B:
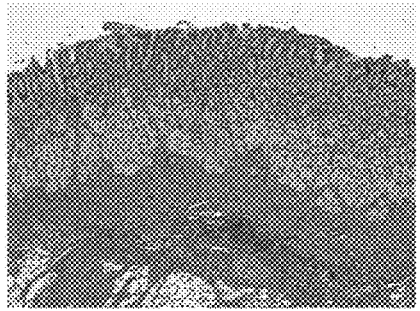
Figure 16C:
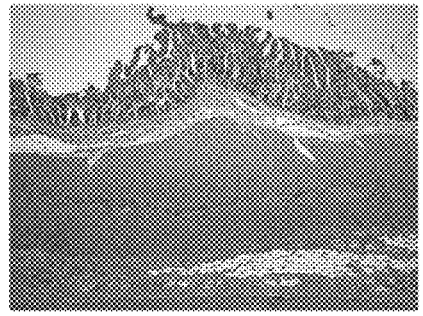

As shown in FIG. 16(A) and FIG. 16(B), no difference between the stomach non-lining part A and the stomach lining part B was found in histological findings, and only slight fibrosis was found in all sites, but the atrophy of the mucous membrane in the stomach was not observed. In addition, as shown in FIG. 16(C) and FIG. 16(D), no difference between the intestinal tract lining part C and the intestinal tract non-lining part D was found in histological findings, and only slight fibrosis was found in all sites, but the atrophy of the gastrointestinal mucosa was not observed. Thus, it was indicated that when the GJIMW device of Example 1 was used, the atrophy of the gastrointestinal mucosa was not caused.

Example 7

The same experiment as that in Example 6 was performed except that the animal in Example 3, which was sacrificed, was used to prepare pathological specimens. Photographs for showing observational results of the pathological specimens of the stomach non-lining part A, the stomach lining part B, the intestinal tract lining part C, and the intestinal tract non-lining part D are shown in FIG. 17(A), FIG. 17(B), FIG. 17(C), and FIG. 17(D), respectively.

Figure 17A:
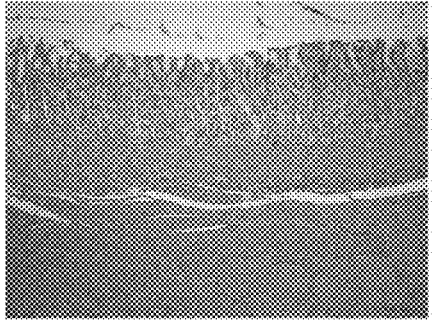
FIG. 17(A), FIG. 17(B), FIG. 17(C), and FIG. 17(D) are photographs for showing observational results of the pathological specimens in Example 7.
Figure 17D:
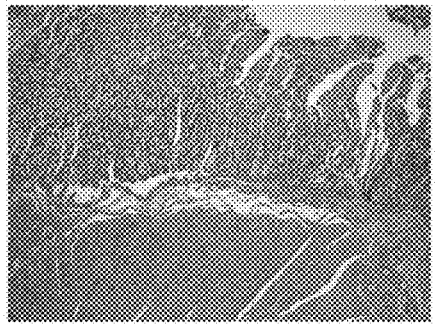
Figure 17B:
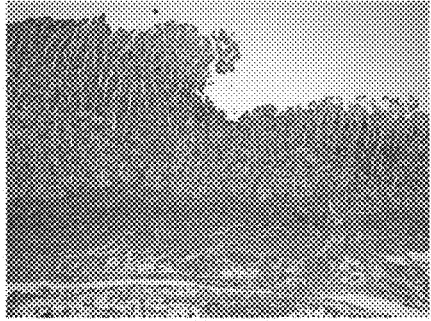
Figure 17C:
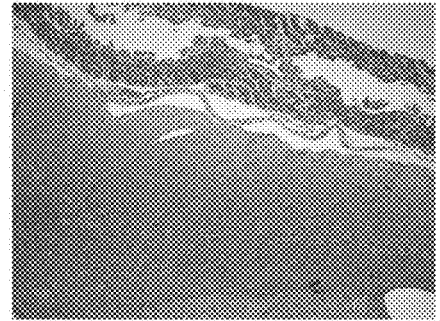

As shown in FIG. 17(A), in the stomach non-lining part A, the atrophy of the mucous membrane of the stomach was not observed. As shown in FIG. 17(B), in the stomach lining part B, only partial erosion, partial thinning of the mucous membrane, and slight inflammation were observed, but the atrophy of the mucous membrane of the stomach was not observed. In addition, as shown in FIG. 17(C) and FIG. 17(D), no difference between the intestinal tract lining part C and the intestinal tract non-lining part D was found in histological findings, and partial erosion, partial thinning of the mucous membrane, and slight inflammation were observed to a similar extent between FIG. 17(C) and FIG. 17(D) in all sites, but the atrophy of the mucous membrane in the intestinal tract was not observed. Thus, it was indicated that when the GJIMW device of Example 3 was used, the atrophy of the gastrointestinal mucosa was not caused.

Example 8

The same experiment as that in Example 6 was performed except that the animal in Example 5, which was sacrificed, was used to prepare pathological specimens. Photographs for showing observational results of the pathological specimens of the stomach non-lining part A, the stomach lining part B, the intestinal tract lining part C, and the intestinal tract non-lining part D are shown in FIG. 18(A), FIG. 18(B), FIG. 18(C), and FIG. 18(D), respectively.

Figure 18A:
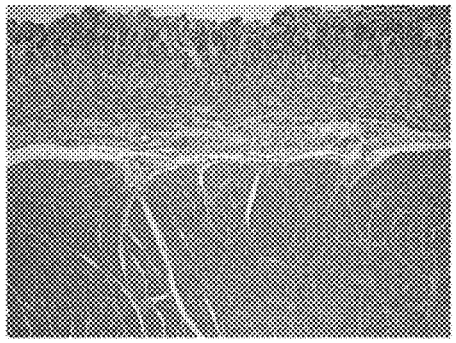
FIG. 18(A), FIG. 18(B), FIG. 18(C), and FIG. 18(D) are photographs for showing observational results of the pathological specimens in Example 8.
Figure 18D:
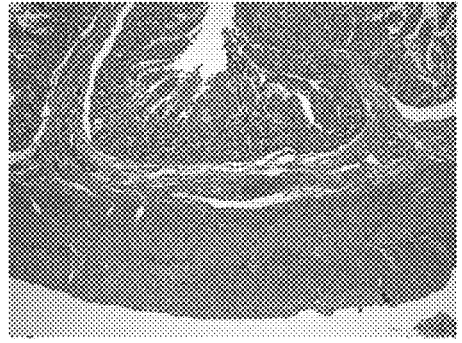
Figure 18B:
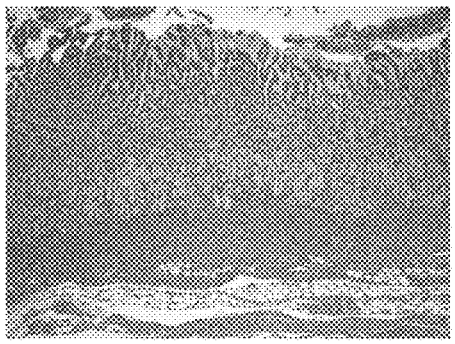
Figure 18C:
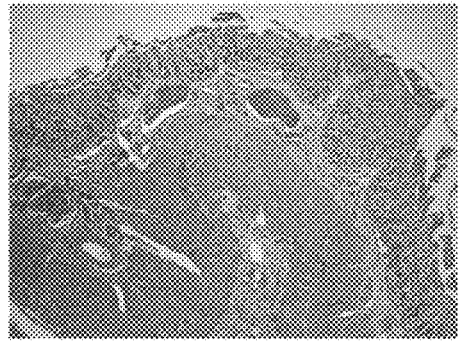

As shown in FIG. 18(A) and FIG. 18(B), no difference between the stomach non-lining part A and the stomach lining part B was found in histological findings, and only slight fibrosis was found in all sites, but the atrophy of the mucous membrane of the stomach was not observed. In addition, as shown in FIG. 18(C) and FIG. 18(D), no difference between the intestinal tract lining part C and the intestinal tract non-lining part D was found in histological findings, and only partial erosion, partial thinning of the mucous membrane, and slight inflammation were observed to a similar extent between FIG. 18(A) and FIG. 18(B) in all sites, but the atrophy of the mucous membrane in the intestinal tract was not observed. Thus, it was indicated that when the GJIMW device of Example 5 was used, the atrophy of the gastrointestinal mucosa was not caused.

As can be seen from the results of Examples 1 to 5, the medical device of the present invention can suppress the digestion and absorption without the atrophy of the gastrointestinal mucosa. In addition, as can be seen from the results of Examples 6 to 8, even when the medical device of the present invention is arranged in a lumen of the gastrointestinal tract, no histological problems including the atrophy of the gastrointestinal mucosa arise. Thus, the medical device of the present invention can suppress the digestion and absorption, and can prevent the atrophy of the gastrointestinal mucosa.

REFERENCE SINGS LIST

10 to 16 medical device
2 attachment part
3 cylindrical part
4 blunt needle with thread
5 esophagus
6 stomach
7 intestinal tract
8 oral cavity
9 endoscope

What is claimed is:

1. A medical device to be arranged in a lumen of a gastrointestinal tract, comprising:
    at least one cylindrical part which is opened at both ends thereof; and
    at least one attachment part which is arranged on at least one portion of the cylindrical part and is configured such that the medical device is attachable to the lumen of the gastrointestinal tract,
    wherein the cylindrical part is configured to be arrangeable along at least one portion of the gastrointestinal tract and has a length of from 30 cm to 9 m, and at least one portion of a side surface of the cylindrical part is configured to be followable to a shape of an inner wall of the gastrointestinal tract and to cause some of a digestive fluid and/or a digested content to permeate therethrough,
    wherein the cylindrical part is deformable in accordance with a motility of the gastrointestinal tract, and
    wherein the cylindrical part is expandable and reducible in a diametrical direction of the cylindrical part in accordance with the motility of the gastrointestinal tract.

2. The medical device according to claim 1, wherein in the cylindrical part, the digested content is brought into contact with a gastrointestinal mucosa.

3. The medical device according to claim 1, wherein a permeable configuration of the cylindrical part comprises at least one shape selected from a net form, a strip form, a slit form, and a perforated form.

4. The medical device according to claim 1, wherein a rate of a cross-sectional area of the cylindrical part at maximum expansion to a cross-sectional area of the cylindrical part is from 200% to 10,000%.

5. The medical device according to claim 1, wherein a rate of a cross-sectional area of the cylindrical part at maximum reduction to a cross-sectional area of the cylindrical part is from 0.5% to 75%.

6. The medical device according to claim 1, wherein the cylindrical part is configured to be unstretchable in a longitudinal direction of the cylindrical part.

7. The medical device according to claim 1, wherein the cylindrical part is expandable and reducible in a diametrical direction of the cylindrical part in accordance with a peristaltic movement of the gastrointestinal tract.

8. The medical device according to claim 1, wherein at least a portion of the cylindrical part has a convex-concave form.

9. The medical device according to claim 1, wherein at least a portion of the cylindrical part is formed of a nonwoven fabric.

10. The medical device according to claim 1, wherein the cylindrical part includes a fixed region having a cross-sectional area of a cross section of the cylindrical part substantially fixed, and an enlargement region extended from the fixed region toward one of the both ends of the cylindrical part and having the cross-sectional area of the cross section of the cylindrical part increased toward one of the both ends of the cylindrical part in a tapered manner.

11. The medical device according to claim 1, wherein the cylindrical part has a length of from 109 cm to 9 m.

* * * * *